United States Patent [19]
Nau et al.

[11] Patent Number: 5,732,708
[45] Date of Patent: Mar. 31, 1998

[54] METHOD FOR STORING EGM AND DIAGNOSTIC DATA IN A READ/WRITE MEMORY OF AN IMPLANTABLE CARDIAC THERAPY DEVICE

[75] Inventors: Peter Nau, Belmont; Lisa M. Clem, Redwood City; Michael O. Williams, Shasta; Glen Crawford, San Francisco, all of Calif.

[73] Assignee: Pacesetter, Inc., Sunnyvale, Calif.

[21] Appl. No.: 689,419

[22] Filed: Aug. 9, 1996

[51] Int. Cl.$^6$ .................................................. A61B 5/0432
[52] U.S. Cl. ............................ 128/710; 128/696; 607/27
[58] Field of Search ................................... 128/696, 710; 607/27, 32

[56] References Cited

U.S. PATENT DOCUMENTS

| | | | |
|---|---|---|---|
| 4,223,678 | 9/1980 | Langer et al. | 128/419 |
| 4,295,474 | 10/1981 | Fischell | 128/697 |
| 4,625,730 | 12/1986 | Fountain et al. | 128/419 |
| 5,012,814 | 5/1991 | Mills et al. | 128/691 |
| 5,086,778 | 2/1992 | Mueller et al. | 128/710 |
| 5,113,869 | 5/1992 | Nappholz et al. | 128/696 |
| 5,312,446 | 5/1994 | Holschbach et al. | 607/9 |
| 5,355,892 | 10/1994 | Saltzstein et al. | 128/710 |
| 5,383,909 | 1/1995 | Keimel | 607/7 |
| 5,413,594 | 5/1995 | Williams | 607/32 |
| 5,487,754 | 1/1996 | Snell et al. | 607/27 |
| 5,513,645 | 5/1996 | Jacobson et al. | 128/710 |
| 5,518,001 | 5/1996 | Snell | 128/697 |
| 5,522,850 | 6/1996 | Yomtov et al. | 607/5 |
| 5,549,654 | 8/1996 | Powell | 607/32 |

FOREIGN PATENT DOCUMENTS

| | | | |
|---|---|---|---|
| 8901803 | 3/1989 | WIPO | A61N 1/362 |

Primary Examiner—William E. Kamm
Assistant Examiner—Kennedy J. Schaetzle
Attorney, Agent, or Firm—Steven M. Mitchell

[57] ABSTRACT

A method for storing digitized electrogram and diagnostic data in a read/write memory of an implantable cardiac therapy device which includes the steps of configuring the memory into first and second memory blocks, configuring the first memory block into a plurality of successive EGM data records for storage of the electrogram data, and the second memory block into a plurality of successive diagnostic data records for storage of the diagnostic data, storing successive electrogram data corresponding to successive EGM trigger events in respective, successive ones of the EGM data records, and, storing successive diagnostic data corresponding to successive diagnostic trigger events in respective, successive ones of the diagnostic data records. The electrogram data is preferably written into the EGM data records in a wraparound, FIFO manner. The memory preferably includes an EGM directory having a plurality of cross-indexed entries each containing several fields of relational data concerning associated ones of the electrogram data records, and a diagnostic directory having a plurality of cross-indexed entries each containing several fields of relational data concerning associated ones of the diagnostic data records, to thereby provide a relational database of electrogram and diagnostic data for subsequent telemetric interrogation by an external instrument.

41 Claims, 2 Drawing Sheets

METHOD FOR STORING EGM AND DIAGNOSTIC DATA IN A READ/WRITE MEMORY OF AN IMPLANTABLE CARDIAC THERAPY DEVICE

BACKGROUND OF THE INVENTION

The present invention relates generally to implantable cardioverter defibrillators, and, more particularly, to a method for optimally configuring and managing electrogram storage memory in such devices, using relational data structures and a novel relational database management scheme.

Implantable cardioverter defibrillators (ICDs) are highly sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle. Cardiac arrhythmias can generally be thought of as disturbances of the normal rhythm of the heart beat. Cardiac arrhythmias are broadly divided into two major categories, namely, bradyarrhythmia and tachyarrhythmia. Tachyarrhythmia can be broadly defined as an abnormally rapid heart rate (e.g., over 100 beats/minute, at rest), and bradyarrhythmia can be broadly defined as an abnormally slow heart rate (e.g., less than 50 beats/minute). Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular. In general, atrial arrhythmias are not life-threatening, because the atria (upper chambers of the heart) are only responsible for aiding the movement of blood into the ventricles (lower chambers of the heart), whereas ventricular arrhythmias are life-threatening, because if the ventricles become arrhythmic, the heart's ability to pump blood to the rest of the body is impaired. The most serious and immediately life-threatening type of cardiac arrhythmia is ventricular fibrillation, in which the electrical activity of the ventricles becomes so random and chaotic that the heart rapidly becomes unable to pump sufficient blood to sustain life.

In general, an ICD continuously monitors the heart activity of the patient in whom the device is implanted by analyzing electrical signals, known as electrograms (EGMs), generated by sensing electrodes positioned proximate the sino-atrial and/or atrio-ventricular node of the patient's heart, and, most advantageously, in the right ventricular apex of the patient's heart. More particularly, contemporary ICDs include waveform digitization circuitry which digitizes the analog EGM produced by the sensing electrodes, and a microprocessor and associated peripheral ICs which analyze the thusly digitized EGM in accordance with a diagnostic algorithm implemented by software stored in the microprocessor. Contemporary ICDs are generally capable of diagnosing the various types of cardiac arrhythmias discussed above, and then delivering the appropriate electrical energy/therapy to the patient's heart, in accordance with a therapy delivery algorithm also implemented in software stored in the microprocessor, to thereby correct or terminate the diagnosed arrhythmia.

In this connection, contemporary ICDs are capable of delivering various types or levels of electrical therapy. The first type of therapy is bradycardia and antitachycardia pacing, in which a low level of electrical energy (generally between millionths to thousandths of a Joule) is delivered to the patient's heart in order to correct detected episodes of bradycardia or tachycardia, respectively. The second type of therapy is cardioversion, in which an intermediate level of electrical energy (generally between 1–5 Joules) is delivered to the patient's heart in order to terminate a detected episode of ventricular arrhythmia (e.g., a detected heart beat in the range of 130–190 beats/minute) or an ongoing episode of tachycardia that antitachycardia pacing has failed to correct or terminate. The third type of therapy is defibrillation, in which a high level of electrical energy (generally above 15 Joules) is delivered to the patient's heart in order to terminate a detected episode of ventricular fibrillation or an episode of ventricular tachycardia which has degraded into ventricular fibrillation due to failure of antitachycardia pacing or cardioversion therapy.

The provision of the above-described different types or levels of therapy is oftentimes referred to in the art as "tiered therapy". In this regard, contemporary ICDs which are capable of delivering tiered therapy are sometimes referred to as combination pacemakers/defibrillators or as implantable cardioverter-defibrillators. As used herein, the terminology "implantable cardiac defibrillator" (ICD) is intended to encompass these and all other forms and types of implantable cardiac devices. Current-generation ICDs which are capable of delivering tiered therapy provide several advantages over previous-generation ICDs which were only capable of delivering high energy defibrillation therapy. Namely, ICDs which are capable of delivering tiered therapy are generally more energy-efficient, since they can deliver much lower energy therapy, such as antitachycardia pacing and cardioversion, to terminate many arrhythmia events before they degrade into a ventricular fibrillation event. The much higher energy defibrillation therapy is only necessary when these lower energy therapies fail to terminate the arrhythmia. Thus, tiered therapy conserves the energy stored in the battery(ies) of the device, thereby extending the longevity of the device, and also enables a significant portion of potential ventricular fibrillation events to be terminated with lower energy therapy which is much less painful and uncomfortable to the patient.

A primary goal in the design and further development of ICDs is to ensure delivery of effective therapy with a minimum expenditure of energy. Reduction of the total energy required to deliver effective therapy enables the size of the batteries and capacitors used in the ICDs to be reduced, thereby enabling a commensurate reduction in the size of the ICD. The benefits to the patient are two-fold. First, the use of lower voltage cardioversion and defibrillation therapy reduces patient pain and discomfort during delivery of such therapy, and second, the reduction in the size of the ICD decreases patient discomfort due to the physical pressure exerted by the ICD within the patient's body. A further benefit is that the longevity of the device can be extended for a given power supply. Additionally, the smaller the ICD, the easier it is to implant the device using minimally invasive surgery, thereby decreasing the cost of implantation. In this regard, it is highly preferable that the ICD be at least small enough to be implanted pectorally, rather than abdominally, without sacrificing functionality, because pectoral implantation requires much less invasive surgery than abdominal implantation. Consequently, pectoral implantation is both much less costly and much more comfortable to the patient (both at the time of implantation and thereafter), than abdominal implantation.

One of the major areas of ongoing R&D within the field of ICDs is the development of increasingly sophisticated diagnostic and therapy delivery algorithms, which enable the above-stated primary ICD design goal to be realized by optimizing the therapeutic efficacy of the device. More particularly, in accordance with the diagnostic algorithm, the microprocessor and associated peripheral ICs continuously monitor the digitized EGMs in order to sense or detect various features thereof, e.g., waveform slope (dv/dt), waveform minima and maxima, intervals between specified cardiac events, etc., which are indicative of various prescribed cardiac events, e.g., QRS complexes, depolarization, repolarization, tachycardia, bradycardia, fibrillation, etc. When a specified cardiac event is detected, the microprocessor, under the control of the therapy delivery algorithm, then triggers and controls the delivery of therapy, e.g., synchronous with (i.e., generally time-related to) such sensed features of the EGMs and/or cardiac events, in order to thereby increase the likelihood for successful therapy (e.g., cardioversion or defibrillation) at any particular energy level, and/or reducing the energy required for successful therapy. In this regard, therapy is generally delivered (by the output or current delivery stage of the ICD, under microprocessor control) as a sequence of one or more electrical pulses, the timing, number, shape, tilt, magnitude, duration, and/or polarity (and/or other characteristics) of which are controlled in accordance with the therapy delivery algorithm in such a manner as to optimize therapeutic efficacy. The optimum values of the parameters or variables used in these algorithms may vary from one patient to the next, depending on the individual patient's particular cardiac condition and/or history.

Another major area of ongoing R&D within the field of ICDs is the development of apparatus and methods for collecting, organizing, collating, assembling, and storing electrogram and diagnostic data in device memory (e.g., RAM). This data can be read out of device memory by using any well-known telemetric read-out or interrogation technique. The patient's physician and other clinical personnel can then use this data to adjust or tweak the values or settings of the parameters used in the diagnostic and shock delivery algorithms, (e.g., by using any well-known technique for telemetrically reprogramming the device), to thereby enable the physician to "customize" the therapy administered by the ICD for that particular patient. Further, such information can aid the physician in gaining a better understanding of the patient's underlying cardiac condition, and the degree to which such condition has benefited from the therapy administered by the ICD, thereby enabling the physician to further refine the modality of treatment of that patient. A database comprised of such data from a population of patients can be compiled for use in clinical and epidemiological studies, and other forms of medical research, to thereby advance the understanding and knowledge of the entire medical community on the subject of human cardiology. In this vein, such a database can be used by clinicians, physicians, medical research scientists, and ICD designers in developing even more efficacious diagnostic and therapy delivery algorithms, and other improvements, for future generations of ICDs.

In connection with the above, U.S. Pat. No. 4,223,678, issued to Langer et al., discloses an ICD which stores electrogram data corresponding to heart activity which occurs before, during, and subsequent to a detected cardiac arrhythmia, for subsequent read-out by the patient's physician or other clinical personnel by a standard telemetric interrogation technique. More particularly, the analog EGM signal from the patient's heart is digitized and stored on a FIFO basis in a first (auxiliary) memory (e.g., a 4K RAM). Then, when a defibrillation or other episode of arrhythmia is detected, the digital EGM data currently stored in the auxiliary memory is frozen, and then, subsequent digital EGM data is stored in a second (main) memory (e.g., a plurality of 4K RAM chips) for a predetermined time period. For example, the auxiliary memory can store 10 seconds of EGM data corresponding to the 10 seconds prior to the detection of the arrhythmia, and the main memory can store the following 70 seconds of EGM data corresponding to the 70 seconds subsequent to detection of the arrhythmia. Time tag data indicating the time and date of the detected arrhythmia can be stored in reserved bit locations in the main memory. EGM and time tag data corresponding to subsequently detected arrhythmic episodes can be stored in separate predesignated portions of the main memory. An episode counter counts the number of detected arrhythmic episodes. During read-out, a multiplexer, under the control of a readout formatter, multiplexes the digital data read out of the device memory, to produce a parallel data stream, which is then converted to a serial data stream by a serial-to-parallel converter. The serial data stream can then be read out telemetrically by an external device.

U.S. Pat. No. 5,012,814, issued to Mills et al., discloses an ambulatory electrocardiogram (ECG) data monitor and recorder which stores digitized ECG and related time data in device memory upon detection of an ICD-produced shock. More particularly, the digitized ECG data is stored in successive scrolling storage buffers within a RAM. Upon detection of a trigger pulse, the digitized ECG data is stored for the duration of a microprocessor-initiated timeout period. Upon lapse of the timeout period, the microprocessor halts the recording of the ECG data, thereby capturing ("capture-storing") the recorded ECG data for subsequent playback or retrieval. The microprocessor then initializes the next scrolling storage buffer, and repeats the process. Thus, the Mills et al. device captures and stores ECG data related in time to occurrences of the ICD-generated pulses.

U.S. Pat. No. 4,295,474, issued to Fischell, discloses an ICD which stores EGM data corresponding to the period immediately prior to, during, and subsequent to a triggering cardiac event, in device memory. The total number of corrective pulses delivered by the ICD, and the total number of triggering cardiac events (e.g., episodes of defibrillation) which occur between successive read-outs of such data are also counted and stored in device memory.

U.S. Pat. No. 5,413,594, issued to Williams, and assigned to the assignee of the present invention, discloses an ICD which stores EGM data and detailed diagnostic data in device memory. The diagnostic data includes cardiac event interval information (e.g., time and duration of each detected arrhythmic episode); information regarding what particular diagnosis was made for each detected arrhythmic episode and what that diagnosis was based on (e.g., that a diagnosis of fibrillation was made based on particular characteristics of the EGM at the time the diagnosis was made); information regarding why therapy was or was not delivered for each detected arrhythmic episode, and information regarding patient response to any such therapy that was delivered; and the number, magnitude, polarity, and duration of the pulses or shocks for each detected arrhythmic episode for which therapy was delivered. The EGM and diagnostic data is correlated in a data frame and is stored for later telemetric transmission to an external instrument, and/or is transmitted in real time to the external instrument. The data frame is decoded by the external instrument for presentation to an attending physician or other clinical personnel in a time-correlated format.

Such detailed diagnostic information enables the physician and/or other clinical personnel to make significantly more precise and accurate determinations regarding device performance and patient response to therapy than was possible with previously known ICDs, and greatly aids the physician in better evaluating the patient's underlying cardiac condition and customizing the therapy delivered by the device. Thus, it can be appreciated that the ICD disclosed in the Williams patent provides much more valuable information to medical researchers, physicians, clinicians, and ICD designers than the limited information provided by previously known ICDs. Further, the ICD disclosed in the Williams patent correlates and interleaves the EGM and diagnostic data in such a manner as to facilitate presentation of such data in a form which is much more useful to the attending physician and/or other clinical personnel. More particularly, the EGM data is preferably displayed on the external readout device as fully annotated EGM data, with the EGM and correlated diagnostic data being displayed together in a manner which is readily comprehensible to the attending physician and/or other clinical personnel, as opposed to the physician having to interpret various unrelated raw EGM data in an oftentimes futile attempt to approximate this diagnostic data, as was required with previously known ICDs.

Although the EGM and diagnostic data storage method disclosed in the above-discussed Williams patent constitutes a significant advancement in the art, there still exists a need in the art for a method of storing such data in a manner which optimizes the utilization of the limited amount of memory which is available in increasingly smaller ICDs for storage of such data, to thereby facilitate the storage of a greater quantity and higher quality of such data, and further, which enhances the accessibility and usability of such data. The present invention fulfills this need.

SUMMARY OF THE INVENTION

The present invention encompasses a method for storing digitized electrogram and diagnostic data in a read/write memory of an implantable cardiac therapy device, which includes the steps of configuring the memory into first and second memory blocks, configuring the first memory block into a plurality of successive EGM data records for storage of the electrogram data, and the second memory block into a plurality of successive diagnostic data records for storage of the diagnostic data, storing successive electrogram data corresponding to successive EGM trigger events in respective, successive ones of the EGM data records, and, storing successive fields of diagnostic data corresponding to successive diagnostic trigger events in respective, successive ones of the diagnostic data records. Diagnostic data records can be independent of and unassociated with any electrogram data records, and electrogram data records can be independent of and unassociated with any diagnostic data records.

The electrogram data is preferably written into the EGM data records in a wraparound, FIFO manner. More particularly, the step of storing successive fields of the electrogram data is preferably carried out by continuously writing electrogram data in a first EGM data record in a wraparound manner, detecting an EGM trigger event, and, in response thereto, generating event marker data indicative thereof, storing the event marker data in the first EGM data record, and then discontinuing the continuously writing sub-step upon filling a prescribed post-trigger data storage portion of the first EGM data record with the electrogram data. The event marker data demarcates a boundary between pre-trigger and post-trigger portions of the electrogram data. The prescribed post-trigger data storage portion of the selected EGM data record preferably has a prescribed length as measured from a storage location of the event marker data. After the first electrogram data field is stored in the first EGM data record, a jump (RAM address change) is made to the EGM data record, and all of the above-recited sub-steps are then repeated. This electrogram data storing process is then repeated for the succeeding ones of the EGM data records.

The electrogram data is preferably stored in the first memory block by wrapping around to the first EGM data record after filling all of the EGM data records with the electrogram data, whereby the oldest electrogram data is replaced by the most recent electrogram data. Similarly, the diagnostic data is preferably stored in the second memory block by wrapping around to the first diagnostic data record after filling all of the diagnostic data records with the diagnostic data, whereby the oldest diagnostic data is replaced by the most recent diagnostic data.

The memory preferably includes an EGM directory having a plurality of cross-indexed EGM directory entries each containing several fields of relational data concerning associated ones of the electrogram data records, and a diagnostic directory having a plurality of cross-indexed diagnostic directory entries each containing several fields of relational data concerning associated ones of the diagnostic data records, to thereby provide a relational database of electrogram and diagnostic data for subsequent telemetric interrogation by an external instrument.

The EGM directory preferably includes a plurality of EGM directory pointers, including an EGM directory current directory entry pointer which contains the address of the EGM directory entry that corresponds to a current electrogram data record currently being stored, and the diagnostic directory preferably includes a plurality of diagnostic directory pointers, including a diagnostic directory current directory entry pointer which contains the address of the current diagnostic directory entry which is currently being written to and that corresponds to a current diagnostic data record currently being stored or to be stored.

The plurality of EGM directory pointers preferably further includes an EGM directory current index pointer which points to the current EGM data record being written to, and the plurality of diagnostic directory pointers preferably further includes a diagnostic directory current index pointer which points to the current diagnostic data record being written to. The plurality of diagnostic directory pointers further includes a current diagnostic data address pointer which is the address of the current diagnostic data record being recorded. There is no corresponding EGM directory pointer because the pointer is in an EGM directory entry field rather than in the EGM directory.

The EGM directory preferably further includes an EGM directory wrap bit which indicates whether all of the EGM data records have been filled and a wraparound to the first one of the EGM data records has occurred, and the diagnostic directory further includes a diagnostic directory wrap bit which indicates whether all of the diagnostic data records have been filled and a wrap around to the first one of the diagnostic data records has occurred.

The EGM relational data stored in each of the successive ones of the EGM directory entries preferably includes EGM timestamp data indicative of the time and date of the EGM trigger event corresponding to the EGM data in the associated electrogram data record, and the diagnostic relational data stored in each of the successive ones of the diagnostic entries preferably includes diagnostic timestamp data indicative of the time and date that an initial diagnosis was made in connection with the diagnostic trigger event corresponding to the diagnostic data in the associated diagnostic data record.

BRIEF DESCRIPTION OF THE DRAWINGS

These and various other features and advantages of the present invention will be more clearly understood from the following detailed description taken in conjunction with the accompanying drawings, in which.

DETAILED DESCRIPTION OF THE INVENTION

Figure 1:
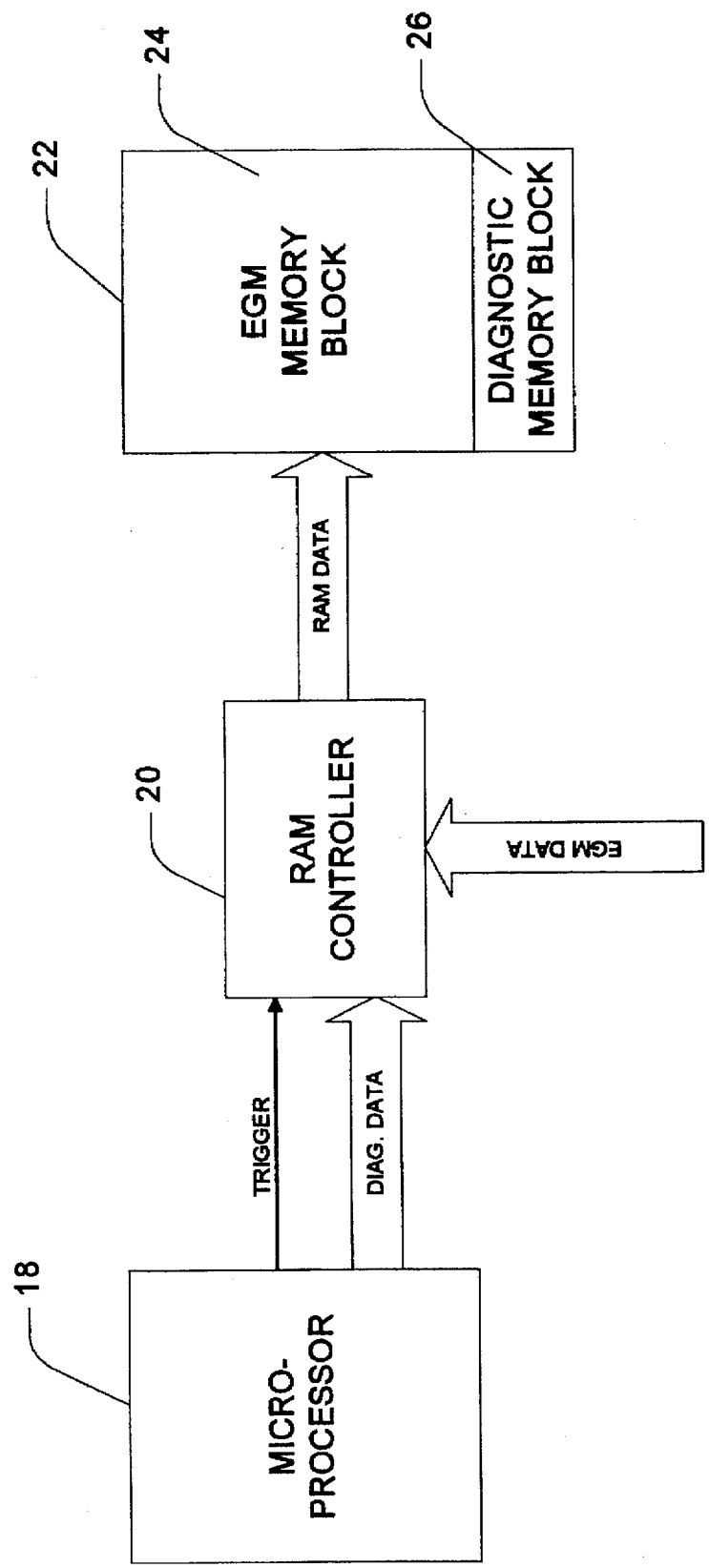
FIG. 1 is a block diagram depicting various elements of an ICD which are utilized in implementing the method of the presently preferred embodiment of the present invention; and, FIG. 2 is a diagrammatic representation of the EGM and diagnostic directories configured in accordance with the presently preferred embodiment of the present invention.

With reference now to FIG. 1, there can be seen a block diagram of a microprocessor 18, a RAM controller 20 and a RAM 22 of an ICD, which may be utilized to implement the data recording or storing method of a presently preferred embodiment of the present invention. In general, RAM controllers are well-known, programmable devices which basically function to write data into and read data from a RAM device consisting of one or more associated RAM chips. The method of the present invention is described in terms of using a generic RAM controller to implement the method, with the understanding that it would be a routine matter for those skilled in the art to select and program a particular RAM controller to carry out the invention.

With continuing reference to FIG. 1, the RAM 22 is organized or configured as follows. First, the RAM 22 is divided into two separate major portions or blocks, namely, an EGM memory block 24 and a diagnostic memory block 26. In this connection, the memory blocks 24 and 26 can either be contained in separate RAM chips, or, in separately allocated portions of the same chip which are dedicated to storage of the two different types of data, i.e., EGM and diagnostic data, respectively. It will be understood that while the division of RAM 22 is discussed in terms of its physical layout, it is a logical division of memory which is occurring. Thus, a memory block may be any designated portion of memory.

Second, the EGM memory block 24 and the diagnostic memory block 26 are each subdivided into a plurality of discrete data records for storage of data pertaining to different trigger events, e.g., cardiac events and/or arrhythmic episodes. Each data record corresponds to a discrete portion of memory which may be of predetermined or variable length. The data stored in each EGM data record can be considered a field or sequence of fields since the data is a sequence of sensed cardiac voltages. The data stored in each diagnostic data record is made up of a plurality of fields each corresponding to a particular piece of information about the diagnosis made by the system and/or therapy delivered. The data records of each memory block 24, 26 may be contained in the same or different memory chips.

Third, separate EGM and diagnostic directories with an array of cross-indexed entries are created in predesignated areas of the RAM 22, for identifying and facilitating more efficient access to the data records in the EGM and diagnostic memory blocks 24 and 26, respectively, to thereby provide a relational database structure. The EGM and diagnostic directories contain a prescribed number (e.g., 60) of separate entries, which are indexed, e.g., from 0 to one less than the prescribed number of entries. Each EGM directory entry is associated with a corresponding EGM data record, and each diagnostic directory entry is associated with a corresponding diagnostic data record. Each directory entry preferably contains several data fields which convey information about the corresponding data record which renders the data more easily and readily accessible, and which enhances the utility thereof. In this regard, the diagnostic directory enables rapid access to important diagnostic information without the overhead of retrieving all diagnostic data for each episode at the same time. In this regard, the attending physician can telemetrically read out all or a selected portion of the diagnostic and/or EGM directory entries, without having to read out all of the EGM and/or diagnostic data records from the RAM 22. The physician can then selectively read out all or a selected portion of a selected one(s) of the EGM and/or diagnostic data records, based upon the read-out directory entry information. This prevents wasted time interrogating all of the data before a presentation of the relevant data can occur. It also prevents problems with communication errors that can occur near the middle or end of a long communication (interrogation) session, which might require the physician to start at the beginning again.

Figure 2:
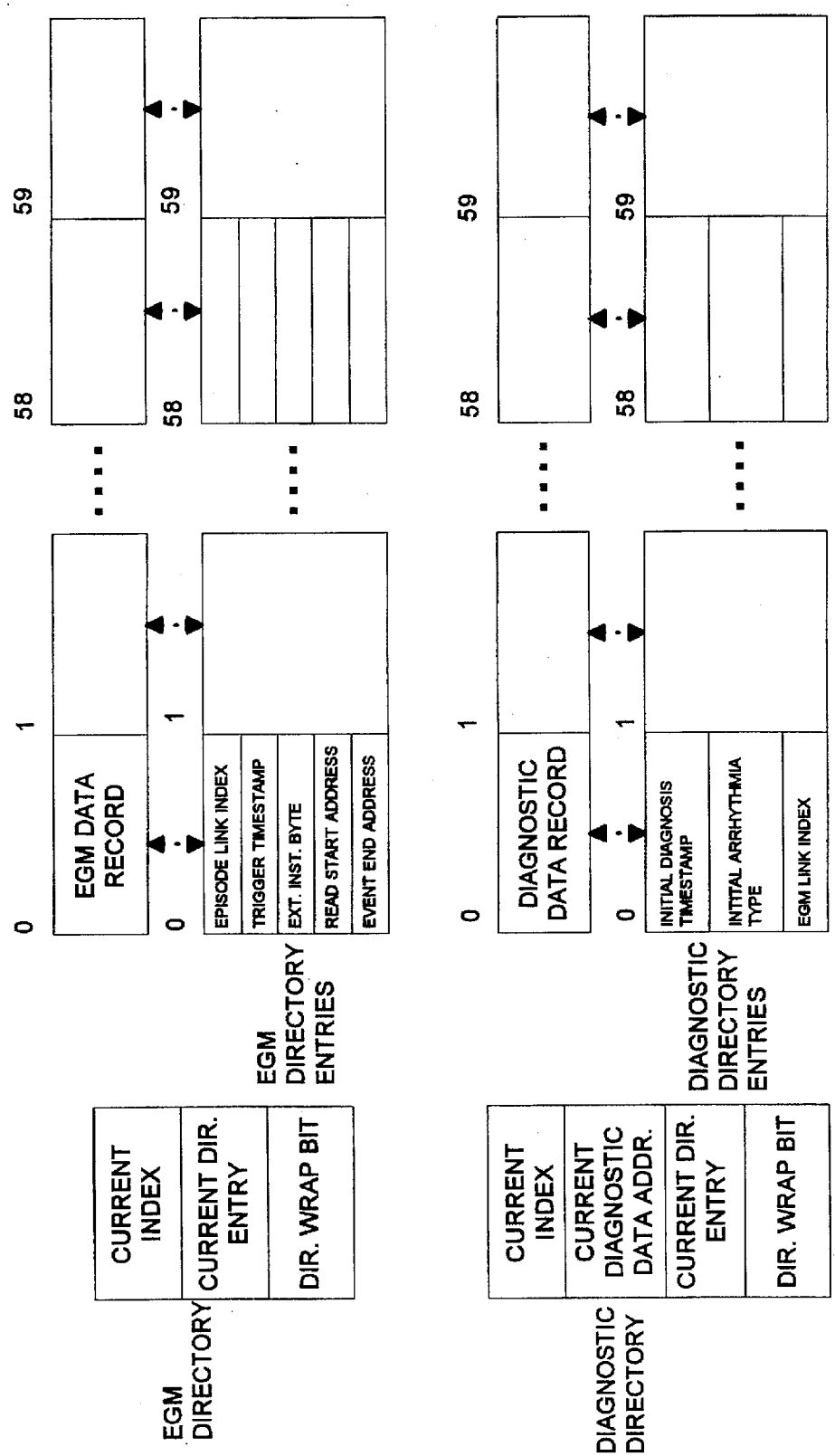

With reference now to FIG. 2, there can be seen a diagrammatic representation of the EGM and diagnostic directories of a presently preferred embodiment of the present invention. As can be seen, each diagnostic directory entry includes three fields, namely, an "Initial Diagnosis Timestamp", an "Initial Arrhythmia Type", and a "Stored EGM Link Index". The "Initial Diagnosis Timestamp" indicates the time and date that the initial diagnosis was made in connection with the episode to which the corresponding diagnostic data record pertains. The "Initial Arrhythmia Type" indicates the type of arrhythmia (e.g., bradycardia, tachycardia A (to be treated with pacing therapy), tachycardia B (to be treated with cardioversion therapy), extended high rate (EHR), fibrillation, etc.) that was initially diagnosed in connection with the episode to which the corresponding diagnostic data record pertains. The "Stored EGM Link Index" indicates the EGM directory entry index (number) corresponding to the EGM data record associated with the episode to which the corresponding diagnostic data record pertains.

With continuing reference to FIG. 2, each EGM directory entry includes five fields, namely, an "Episode Link Index", a "Trigger Timestamp", an "External Instrument Byte", a "Read Start Address", and an "Event End Address". The "Episode Link Index" indicates the diagnostic directory entry index (number) of the diagnostic data record associated with the episode to which the corresponding EGM data record pertains. The "Trigger Timestamp" indicates the time and date of the trigger signal (i.e., trigger event) which triggered the storage of the corresponding EGM data record. The "External Instrument Byte" indicates whether the corresponding EGM data record has been previously interrogated (i.e., telemetrically read out) by an external instrument. The "Read Start Address" indicates the starting address of the corresponding EGM data record for read-out thereof, and the "Event End Address" indicates the ending address of the corresponding recorded EGM data for read-out thereof.

With continuing reference to FIG. 2, the EGM and diagnostic directories each preferably further include an array of pointers. More particularly, the EGM directory preferably includes a current index pointer which points to the EGM directory entry that corresponds to the episode in progress (if any), and a current directory entry pointer which is the address of the EGM directory entry which is currently being written to and that corresponds to the EGM data record presently being recorded. The diagnostic directory preferably includes a current index pointer which points to the diagnostic directory entry that corresponds to the episode in progress (if any), a current directory entry pointer which is the address of the diagnostic directory entry which is currently being written to and that corresponds to the diagnostic data record presently being recorded (or to be recorded), and a current diagnostic data record pointer which contains the address of the diagnostic data record presently being recorded.

In the presently preferred embodiment of the present invention, the diagnostic and EGM directories can be programmed to store a maximum number of entries, e.g., 60. In this regard, the programmed maximum number of diagnostic directory entries and the programmed maximum number of EGM directory entries need not be the same. Further, the diagnostic directory and the EGM directory can be erased (cleared) independently of one another. Erasure of either directory can be accomplished by resetting the current index pointer to the first data record, and by clearing a directory "wrap bit". The directory "wrap bit" is a directory flag which indicates that the directory and corresponding data records have been filled (i.e., the last directory entry and data record have been recorded), and the current index pointer has wrapped around to the first directory entry and data record at least once, and that old directory entries and data records are being written over by new directory entries and data records.

Although the above-described directory entries and pointers are presently preferred, it should be clearly understood that the number and type of directory entries and pointers employed in the practice of the present invention is not limiting thereto.

Although the entries are preferably cross-indexed, as described above, there need not be a one-to-one correspondence between the EGM data records in the EGM memory block 24 and the data records in the diagnostic memory block 26. In other words, EGM data can be stored in the EGM memory block 24 which is independent from and unassociated with any diagnostic data stored in the diagnostic memory block 26, and diagnostic data can be stored in the diagnostic memory block 26 which is independent from and unassociated with any EGM data stored in the EGM memory block 24. For example, in accordance with one aspect of the present invention, if an arrhythmic event is detected and initially diagnosed as an incipient arrhythmic episode, but a return to sinus (normal) rhythm is detected before any therapy is delivered (i.e., therapy is not initiated or is terminated), then the EGM data corresponding to this event will be discarded (i.e., not permanently stored in the current EGM data record), but the diagnostic data corresponding to this event may be permanently stored in the current diagnostic data record. In this case, there will be no EGM entry in the EGM directory corresponding to the diagnostic data entry in the diagnostic directory. Such an arrhythmic event may be thought of as a "potential episode". If the arrhythmic event is ultimately diagnosed as an "actual" arrhythmic episode (i.e., therapy is delivered), then the EGM data corresponding to this episode will be permanently stored (until it is overwritten or cleared) in the current EGM data record, and thus, there will be corresponding, bidirectionally cross-indexed entries in both the EGM and diagnostic directories.

Similarly, in accordance with another aspect of the present invention, it is possible to store EGM data corresponding to a non-episodal trigger event in the current EGM data record, in which case, there will not be any associated diagnostic data to store in the current diagnostic data record. Exemplary non-episodal trigger events include magnet reversion, noise reversion, commanded shock and forced electrogram store events. In the case of a non-episodal trigger event, there will be no diagnostic data entry in the diagnostic directory corresponding to the EGM data entry in the EGM directory. In this regard, the RAM controller 20 can be programmed to store a maximum number of electrograms for each type of non-episodal event, e.g., a maximum of one each of magnet and noise reversion electrograms, since the recordation of electrograms for non-episodal events may limit the number of more desirable electrograms pertaining to arrhythmic episodes.

In accordance with another aspect of the presently preferred embodiment of the present invention, a determination can be made whether cross-index links between the EGM and diagnostic directories are valid in accordance with the following validity test, preferably while data is being read from the RAM 22. Namely, the links are valid only if:

(1) they are bi-directional, meaning that if the Episode Link Index in the mth entry in the EGM directory points to the nth entry in the diagnostic directory, then the EGM Link Index in the nth entry in the diagnostic directory must point to the mth entry in the EGM directory; and, (2) both of the cross-indexed entries are valid. In this regard, if the directory "wrap bit" in the EGM directory is set, then all entries in the EGM directory except for the current entry are valid, and if the directory "wrap bit" in the diagnostic directory is set, then all entries in the diagnostic directory except for the current entry are valid. If the directory "wrap bit" is not set, then only the entries in the respective directory prior to the current directory entry are valid.

For reasons which will become fully apparent hereinafter, the capability of storing independent, unassociated EGM and diagnostic data provides an additional dimension of flexibility to the storage of EGM and diagnostic data in an ICD relative to the presently available technology, and greatly enhances the accessibility and utility of such data.

In accordance with the method of the presently preferred embodiment of the present invention, the RAM controller 20 is programmed to function in the following manner to control the storage (and readout) of diagnostic data produced by the microprocessor 18 and digitized EGM data, e.g., in the manner taught by the above-discussed Williams patent (U.S. Pat. No. 5,413,594), the disclosure of which is herein incorporated by reference. During periods between detection of trigger events, e.g., arrhythmic events or episodes, the RAM controller 20 continuously stores the digitized EGM data in a selected EGM data record which is identified in the current index pointer. Of course, prior to the first detection of an arrhythmic or other trigger event, the current index pointer will point (indirectly) to the first EGM data record. In this connection, the digitized EGM data is stored, sample-by-sample, until the selected EGM data record is filled. When the selected EGM data record is filled, the most recently obtained sample of digitized EGM data is recorded (written) over the oldest sample. This data storage technique is sometimes referred to as a "wrap around" technique, since the digitized EGM data is continuously recorded in a wrap-around or circular fashion, beginning with the starting address of the selected EGM data record and continuing until the ending address of the selected EGM data record is reached, at which point, the previously recorded data is written over (i.e., replaced) with the most recent data, beginning with the starting address, and the process is repeated, until a trigger event is detected. Thus, each EGM data record can be considered to constitute a scrolling or circulating data storage buffer, with the data being written thereinto on a FIFO (first-in, first-out) basis.

When the microprocessor 18 detects the occurrence of an arrhythmic or other trigger event (e.g., bradycardia, tachycardia A (to be treated with pacing therapy), tachycardia B (to be treated with cardioversion therapy), extended high rate (EHR), fibrillation, etc.), it generates a trigger signal which is applied as an input to the RAM controller 20. The trigger signal is preferably encoded to indicate the type of trigger event which caused it to be generated by the microprocessor 18. The RAM controller 20 is also programmed to generate event marker data in response to change-in-status events, e.g., delivery of therapy, depolarization, return to sinus rhythm, and other cardiac and/or device change-in-status events). The event marker data is preferably encoded to provide information about the change-in-status event which triggered the recordation of the event marker data. The event marker data is recorded in the EGM data records in the same manner as is the digitized EGM data, as described hereinabove. In that case, the EGM data sample corresponding to the time of the event marker data may be discarded or written over by the event marker data.

The RAM controller 20 can be programmed to set the length of the post-trigger EGM data storage portion of the EGM data records to any desired length not greater than the total length (i.e., ending address minus starting address) of the EGM data records. In this regard, the EGM data received following receipt of a trigger signal is preferably written into the current EGM data record until a prescribed number of bytes or addressable storage locations of the current EGM data record are filled with post-trigger EGM data, even if this requires a wraparound. This process is sometimes referred to as an "event store". As will be evident to those skilled in the art, the post-trigger EGM data storage portion of the current EGM data record is comprised of the portion of the current EGM data record extending from the starting address of the post-trigger EGM data to an ending address, where the absolute difference of the ending address minus the starting address equals the length of the post-trigger EGM data portion of the current EGM data records. Preferably, the length of the post-trigger EGM data storage portion of the EGM data records is selected to provide a pre-trigger EGM data storage portion of suitable length. In this connection, the length of the pre-trigger EGM data storage portion of the EGM data records is equal to the absolute value of the total length of the EGM data records minus the length of the post-trigger EGM data storage portion of the EGM data records. Alternatively, EGM data can be written into the current EGM data record for a prescribed period of time following receipt of a trigger pulse, to achieve the same result. It should be clearly understood, however, that the lengths of the pre-trigger and post-trigger data storage portions of the EGM data records are preferably fully programmable to any desired value, i.e., from 0 to a prescribed maximum.

In the presently preferred embodiment of the present invention, the RAM controller 20 can be programmed to halt the recording of post-trigger EGM data in response to an end-of-event command generated by the microprocessor 18 upon detection that the trigger event which triggered the event store process described above has terminated. For example, if the trigger event was a detected arrhythmic episode, e.g., fibrillation, which has been successfully terminated by therapy, e.g., defibrillation shock therapy, delivered by the ICD, then an end-of-event command would be generated by the microprocessor 18. Upon receipt of an end-of-event command, the RAM controller 20 preferably writes a special marker data byte generated by the microprocessor 18 into the next byte of the current EGM data record. This special marker data byte indicates the end of valid data in the post-trigger EGM data storage portion of the current EGM data record. The end-of-event command will be ignored by the RAM controller 20 unless an event store is in progress.

After the post-trigger EGM data is stored in the current EGM data record (i.e., the event store is completed), the current index pointer in the EGM directory is incremented or advanced to the next EGM data record, and the incoming EGM data is continuously recorded in a wrap-around or circular fashion, as with the previous EGM data record. When the next trigger signal is received by the RAM controller 20, the event marker data and post-trigger EGM data are stored in the same manner as described above in connection with the previous EGM data record. This process is repeated until all of the EGM data records in the EGM memory block 24 are filled. At this point, in accordance with another aspect of the present invention, the current index pointer is advanced to the first EGM data record, and the current EGM data is then written over the EGM data record previously stored therein. In other words, after the last EGM data record has been filled, i.e., the end of the available memory space in the EGM memory block 24 of the RAM 22 has been reached, the RAM controller 20 will wrap around to the first EGM data record. Thus, the most current EGM data will replace the oldest EGM data recorded in the EGM memory block 24, data record-by-data record. As such, the entire EGM memory block 24 can be considered to be an array or collection of FIFO memory records. A special bit(s), hereinafter referred to as the EGM directory "wrap bit", is preferably stored in the EGM directory, to indicate that a wraparound has occurred. In the presently preferred embodiment of the present invention, the EGM data element wrap bit is stored in the current EGM data element pointer in the EGM directory. In this manner, when the EGM data is subsequently read out of the EGM memory block 24, the read-out device (e.g., an external instrument) will be able to easily determine which is the last (most recently recorded) EGM data record, and which is the first (earliest recorded) EGM data record, and will also be able to easily determine whether or not the read-out EGM data is valid.

Diagnostic data generated by the microprocessor 18 is preferably written into successive diagnostic data records of the diagnostic memory block 26 by the RAM controller 20 on an episode-by-episode basis. In this connection, each of the diagnostic data records preferably includes a plurality of fields for storage of different types of diagnostic data that may be generated by the microprocessor 18 during an episode. When all of the diagnostic data records in the diagnostic memory block 26 are filled, the current index pointer in the diagnostic directory is advanced to the first diagnostic data record, and the current diagnostic data is then written over the diagnostic data record previously stored therein. In other words, after the last diagnostic data record has been filled, i.e., the end of the available memory space in the diagnostic memory block 26 has been reached, the RAM controller 20 will wrap around to the first diagnostic data record. Thus, the most recent diagnostic data will replace the oldest diagnostic data recorded in the diagnostic memory block 26, data record-by-data record, until the diagnostic data is telemetrically read out by an external instrument and/or the diagnostic memory block 26 is cleared. As such, the entire diagnostic memory block 26 can be considered to be a FIFO memory. A special bit(s), hereinafter referred to as the diagnostic directory "wrap bit", is preferably stored in the diagnostic directory, to indicate that a wraparound has occurred. In the presently preferred embodiment of the present invention, the diagnostic directory wrap bit is stored in the current diagnostic data address pointer in the diagnostic directory, e.g., as a "don't care bit" of the current diagnostic data address. In this manner, when the diagnostic data is subsequently read out of the diagnostic memory block 26, the read-out device (e.g., an external instrument) will be able to easily determine which is the last (most recently recorded) diagnostic data record, and which is the first (earliest recorded) diagnostic data record, and will also be able to easily determine whether or not the read-out diagnostic data is valid.

Although the type of diagnostic data recorded in the diagnostic memory block 26 is not limiting to the present invention, in its broadest sense it is preferable that this data at least include the type of initial trigger event which was detected to initiate an EGM event store cycle, the initial diagnosis which was made, the type of initial therapy which was attempted (if any), and whether therapy was aborted due to redetection of sinus rhythm (i.e., an arrhythmic trigger event was ultimately determined to be a potential episode, as opposed to an actual arrhythmic episode) or because the initial diagnosis was incorrect. Preferably, the diagnostic data will include additional detailed diagnostic information about each detected arrhythmic episode, such as the type of diagnostic information disclosed in the Williams patent (U.S. Pat. No. 5,413,594), e.g., the reasons why the initial diagnosis was made, whether any further diagnoses were made, and, if so, why; the number, magnitude, polarity, and/or duration of any pulses or shocks delivered as therapy; information regarding why therapy was or was not delivered; and, information regarding patient response to any such therapy that was delivered.

Although a presently preferred embodiment of the present invention has been described in detail hereinabove, it should be clearly understood that many variations and/or modifications of the basic inventive concepts herein taught which may appear to those skilled in the pertinent art will still fall within the spirit and scope of the present invention, as defined in the appended claims. For example, although the preferred embodiment of the present invention has been described above in terms of using and storing electrograms, oftentimes referred to as EGMs, produced by internal sensing electrodes, it should be clearly understood that the invention has equal applicability to the use and storage of electrocardiograms, oftentimes referred to as ECGs, produced by skin or surface electrodes placed on the patient's chest. In this connection, the term "EGM" is intended to encompass electrograms produced by internal and/or external sensing electrodes. Thus, the device can be implanted or external, and it may deliver therapy or just monitor and diagnose the heart. Moreover, it is possible to store EGM data corresponding to two or more different events which occur during a single arrhythmic episode in two or more respective EGM data records, and thus, have two or more EGM directory entries linked to the same diagnostic directory entry, and vice versa. For example, after an arrhythmic episode is initially detected, and the EGM data pertaining thereto is recorded in an EGM data record, subsequent EGM data pertaining to subsequent detected events which occur while the episode is in progress, e.g., delivery of initial therapy, initial diagnosis, detection of sinus rhythm, and the like, can be recorded in succeeding EGM data records. In this connection, the RAM controller 20 can be programmed to store electrograms for any combination of events which occur during episodes and/or arrhythmic events. Furthermore, it is possible to provide EGM data records and diagnostic data records of variable length.

What is claimed is:

1. A method for storing digitized electrogram and diagnostic data in a read/write memory of an implantable cardiac therapy device, including the steps of:

configuring the memory into first and second memory blocks;

configuring said first memory block into a plurality of successive EGM data records for storage of said electrogram data, and said second memory block into a plurality of successive diagnostic data records for storage of said diagnostic data;

storing successive electrogram data corresponding to successive EGM trigger events in respective, successive ones of said EGM data records;

storing successive diagnostic data corresponding to successive diagnostic trigger events in respective, successive ones of said diagnostic data records; and storing in an EGM directory a plurality of successive EGM entries associated with respective ones of said EGM data records.

2. The method as set forth in claim 1 and further including the step of storing EGM relational data concerning associated ones of said electrogram data records in successive ones of said EGM entries.

3. The method as set forth in claim 2, wherein said EGM relational data stored in each of said successive ones of said EGM entries includes EGM timestamp data indicative of the time and date of said EGM trigger event corresponding to the associated electrogram data record.

4. The method as set forth in claim 1, wherein the step of storing successive electrogram data includes the sub-steps of continuously writing said electrogram data in a selected one of said EGM data records in a wraparound manner;

detecting an EGM trigger event, and in response thereto, discontinuing the continuously writing sub-step upon filling a post-trigger data storage portion of said selected EGM data record with a post-trigger portion of said electrogram data; and, repeating each of the above-recited sub-steps for successive ones of said EGM data records.

5. The method as set forth in claim 4, wherein the step of storing successive records of said electrogram data further includes the sub-step of generating end-of-event marker data in response to detection of an end of said EGM trigger event, and storing said end-of-event marker data in a storage location of said selected EGM data record next to a last byte of said post-trigger portion of said electrogram data.

6. The method as set forth in claim 1, wherein the step of storing successive electrogram data includes the sub-steps of:

continuously writing said electrogram data in a selected one of said EGM data records in a wraparound manner;

detecting change-in-status events, and in response thereto, generating event marker data indicative thereof, and storing said event marker data in said selected EGM data record;

detecting an EGM trigger event, and in response thereto, discontinuing the continuously writing sub-step upon filling a prescribed post-trigger portion of said selected EGM data record with a post-trigger portion of said electrogram and event marker data; and, repeating each of the above-recited sub-steps for successive ones of said EGM data records.

7. The method as set forth in claim 1, wherein:

each of said EGM data records has a prescribed length as measured from its starting address to its ending address; and, each of said diagnostic data records has a prescribed length as measured from its starting address to its ending address.

8. The method as set forth in claim 1, wherein each of said successive diagnostic data records is comprised of a plurality of fields each containing a different type of diagnostic data.

9. The method as set forth in claim 1, wherein the step of storing successive electrogram data is carried out by wrapping around to the first one of said EGM data records after filling all of said EGM data records with said electrogram data, whereby the oldest electrogram data is replaced by the most recent electrogram data.

10. The method as set forth in claim 1, wherein the step of storing successive diagnostic data is carried out by wrapping around to the first one of said diagnostic data records after filling all of said diagnostic data records with said diagnostic data, whereby the oldest diagnostic data is replaced by the most recent diagnostic data.

11. A method for storing digitized electrogram and diagnostic data in a read/write memory of an implantable cardiac therapy device, including the steps of:

configuring the memory into first and second memory blocks;

configuring said first memory block into a plurality of successive EGM data records for storage of said electrogram data, and said second memory block into a plurality of successive diagnostic data records for storage of said diagnostic data;

storing successive electrogram data corresponding to successive EGM trigger events in respective, successive ones of said EGM data records;

storing successive diagnostic data corresponding to successive diagnostic trigger events in respective, successive ones of said diagnostic data records; and storing in a diagnostic directory a plurality of successive diagnostic entries associated with respective ones of said diagnostic data records.

12. The method as set forth in claim 11, and further including the step of storing diagnostic relational data concerning associated ones of said diagnostic data records in successive ones of said diagnostic entries.

13. The method as set forth in claim 12, wherein said diagnostic relational data stored in each of said successive ones of said diagnostic entries includes diagnostic timestamp data indicative of the time and date that an initial diagnosis was made in connection with said diagnostic trigger event corresponding to the associated diagnostic data record.

14. A method for storing digitized electrogram and diagnostic data in a read/write memory of an implantable cardiac therapy device, including the steps of:

configuring the memory into first and second memory blocks;

configuring said first memory block into a plurality of successive EGM data records for storage of said electrogram data, and said second memory block into a plurality of successive diagnostic data records for storage of said diagnostic data;

storing successive electrogram data corresponding to successive EGM trigger events in respective, successive ones of said EGM data records;

storing successive diagnostic data corresponding to successive diagnostic trigger events in respective, successive ones of said diagnostic data records;

storing in a diagnostic directory a plurality of successive diagnostic entries associated with respective ones of said diagnostic data records;

storing in an EGM directory a plurality of successive EGM entries associated with respective ones of said EGM data records;

storing EGM relational data concerning associated ones of said electrogram data records in successive ones of said EGM entries, said EGM relational data stored in each of said successive ones of said EGM entries including diagnostic link index data identifying a linked diagnostic entry, if any, associated with said EGM entry; and storing diagnostic relational data concerning associated ones of said diagnostic data records in successive ones of said diagnostic entries, said diagnostic relational data stored in each of said successive ones of said diagnostic entries including EGM link index data identifying a linked EGM entry, if any, associated with said diagnostic entry.

15. The method as set forth in claim 14, wherein said diagnostic relational data stored in each of said successive ones of said diagnostic entries further includes initial diagnosis data indicative of the initial diagnosis that was made in connection with said diagnostic trigger event corresponding to the associated diagnostic data record.

16. The method as set forth in claim 14, wherein said EGM relational data stored in each of said successive ones of said EGM entries further includes data identifying the storage location of the associated diagnostic data record.

17. The method as set forth in claim 14, wherein:

said EGM directory includes a plurality of EGM directory pointers, including an EGM directory current directory entry pointer which points to a current EGM directory entry that corresponds to a current electrogram data record currently being stored; and, said diagnostic directory includes a plurality of diagnostic directory pointers, including a diagnostic directory current directory entry pointer which points to a current diagnostic directory entry that corresponds to a current diagnostic data record currently being stored or to be stored.

18. The method as set forth in claim 17, wherein:

said plurality of EGM directory pointers further includes an EGM directory current index pointer which points to said current EGM directory entry; and, said plurality of diagnostic directory pointers further includes a diagnostic directory current index pointer which points to said current diagnostic directory entry.

19. The method as set forth in claim 17, wherein:

said plurality of diagnostic directory pointers further includes a current diagnostic data address pointer which points to said current diagnostic data record.

20. The method as set forth in claim 14, wherein said step of storing successive electrogram data is carried out by wrapping around to the first one of said EGM data records after filling all of said EGM data records with said electrogram data, whereby the oldest electrogram data is replaced by the most recent electrogram data, said EGM directory including an EGM directory wrap bit which indicates whether all of said EGM data records have been filled and a wrap around to said first one of said EGM data records has occurred.

21. The method as set forth in claim 14, wherein the step of storing successive diagnostic data is carried out by wrapping around to the first one of said diagnostic data records after filling all of said diagnostic data records with said diagnostic data, whereby the oldest diagnostic data is replaced by the most recent diagnostic data, said diagnostic directory including a diagnostic directory wrap bit which indicates whether all of said diagnostic data records have been filled and a wrap around to said first one of said diagnostic data records has occurred.

22. The method as set forth in claim 14, wherein said step of storing diagnostic relational data includes storing at least one of said diagnostic data records independent of and unassociated with any of said electrogram data records.

23. The method as set forth in claim 14, wherein said step of storing EGM relational data includes storing at least one of said electrogram data records independent of and unassociated with any of said diagnostic data records.

24. A method for storing digitized electrogram and diagnostic data in a read/write memory of a cardiac device, comprising the steps of:

storing said digitized electrogram and diagnostic data in separate storage locations in said memory, as a plurality of separate electrogram data records and diagnostic data records; and, storing relational data identifying said separate storage locations of related ones of said electrogram data records and diagnostic data records.

25. The method as set forth in claim 24, wherein at least one of said electrogram data records and diagnostic data records are unrelated.

26. The method as set forth in claim 24, further comprising the step of reading said relational data from the memory and then reading one or more selected ones of said electrogram and/or diagnostic data records from the memory based upon said relational data read from the memory.

27. The method as set forth in claim 24, wherein said relational data also identifies diagnostic data records and/or electrogram data records which are unrelated to any other stored data records of either type.

28. The method as set forth in claim 24, further comprising the step of determining the validity of the stored electrogram data records and/or diagnostic data records.

29. The method as set forth in claim 24, wherein said relational data further includes time and date data associated with each of said electrogram and diagnostic data records, and further comprising the step of reading said relational data from the memory and then reading one or more selected ones of said electrogram data records and/or diagnostic data records from the memory based upon said relational data read from the memory.

30. A method for storing digitized electrogram and diagnostic data in a read/write memory of a cardiac device, comprising the steps of:

storing said digitized electrogram and diagnostic data in the memory as a plurality of separate electrogram data records and diagnostic data records; and, creating a directory containing identification data regarding each of said electrogram data records and diagnostic data records.

31. The method as set forth in claim 30, wherein said directory is comprised of an electrogram directory containing electrogram identification data regarding each of said electrogram data records, and a diagnostic directory containing diagnostic identification data regarding each of said diagnostic data records.

32. The method as set forth in claim 31, further comprising the step of reading said electrogram identification data and said diagnostic identification data from the memory, and then reading one or more selected ones of said electrogram data records and/or diagnostic data records from the memory based upon said electrogram identification data and diagnostic identification data read from the memory.

33. The method as set forth in claim 31, wherein said electrogram and diagnostic directories are cross-indexed.

34. The method as set forth in claim 31, wherein said diagnostic identification data includes diagnostic timestamp data indicative of the time and date that each of said diagnostic data records was stored in the memory.

35. The method as set forth in claim 31, wherein said electrogram identification data includes electrogram timestamp data indicative of the time and date that each of said electrogram data records was stored in the memory.

36. The method as set forth in claim 31, wherein said diagnostic identification data further includes electrogram link index data identifying a linked electrogram data record, if any, for each of the stored diagnostic data records.

37. The method as set forth in claim 31, wherein said electrogram identification data further includes diagnostic link index data identifying a linked diagnostic data record, if any, for each of the stored electrogram data records.

38. The method as set forth in claim 31, wherein said electrogram identification data further includes electrogram record address data identifying the storage location in the memory for each of said electrogram data records.

39. The method as set forth in claim 31, wherein said diagnostic identification data further includes diagnostic record address data identifying the storage location in the memory for each of said diagnostic data records.

40. The method as set forth in claim 37, wherein said diagnostic identification data further includes electrogram link index data identifying a linked electrogram data record, if any, for each of the stored diagnostic data records and further comprising the step of determining the validity of cross-linked ones of said electrogram data records and diagnostic data records, if any, by determining if there is bi-directional correspondence between said electrogram link index data and said diagnostic link index data.

41. The method as set forth in claim 31, wherein said diagnostic identification data includes initial diagnosis data, initial arrhythmia type data, and initial diagnosis timestamp data, and further comprising the step of reading at least a selected portion of said diagnostic identification data from the memory, and then reading one or more selected ones of said electrogram records and/or diagnostic data records from the memory based upon said selected portion of said diagnostic identification data.

* * * * *